United States Patent
Alfouzan

(10) Patent No.: US 9,801,461 B1
(45) Date of Patent: Oct. 31, 2017

(54) ELECTRIC TOOTHBRUSH HOLDER FOR LABORATORY USE

(71) Applicant: KING SAUD UNIVERSITY, Riyadh (SA)

(72) Inventor: Afnan Fouzan Alfouzan, Riyadh (SA)

(73) Assignee: KING SAUD UNIVERSITY, Riyadh (SA)

( * ) Notice: Subject to any disclaimer, the term of this patent is extended or adjusted under 35 U.S.C. 154(b) by 0 days.

(21) Appl. No.: 15/378,007

(22) Filed: Dec. 13, 2016

(51) Int. Cl.
*A46B 17/02* (2006.01)
*A47K 1/09* (2006.01)
*A61C 17/00* (2006.01)
*A61C 17/22* (2006.01)

(52) U.S. Cl.
CPC ........... *A46B 17/02* (2013.01); *A47K 1/09* (2013.01); *A61C 17/036* (2013.01); *A61C 17/22* (2013.01)

(58) Field of Classification Search
CPC ........ A46B 17/02; A47K 1/09; A61C 17/036; A61C 17/22; A61C 19/04; A61C 19/02; A61C 9/0093; G01N 3/56; A47F 7/0035; A47G 29/08; A61B 17/02
USPC ........................................ 248/110–113; 73/7
See application file for complete search history.

(56) References Cited

U.S. PATENT DOCUMENTS

| | | | |
|---|---|---|---|
| 3,929,001 A * | 12/1975 | Lee | G01N 3/56 73/7 |
| 3,942,194 A | 3/1976 | Winter | |
| 4,698,507 A * | 10/1987 | Tator | G01N 17/00 250/429 |
| 4,728,071 A | 3/1988 | Salacuse | |
| 4,903,534 A * | 2/1990 | Kane | G01N 3/56 73/865.9 |
| 9,155,382 B2 | 10/2015 | Duffner | |
| 2011/0232361 A1* | 9/2011 | Schlueter | G01M 99/008 73/7 |
| 2012/0112018 A1 | 5/2012 | Barry et al. | |
| 2015/0129522 A1 | 5/2015 | Werden | |

* cited by examiner

*Primary Examiner* — Christopher E Garft
(74) *Attorney, Agent, or Firm* — Richard C. Litman

(57) ABSTRACT

The electric toothbrush holder for laboratory use is a holder for the testing of dental appliances. The electric toothbrush holder for laboratory use includes a base having opposed upper and lower surfaces. A sample receptacle is mounted on the upper surface of the base and defines an open interior region for removably receiving a dental sample. At least one support is mounted on the upper surface of the base for releasably supporting a gripping portion of an electric toothbrush. At least one bracket is pivotally secured to the at least one support for releasably securing the gripping portion of the electric toothbrush to the at least one support. In use, the gripping portion of the electric toothbrush is releasably secured to the at least one support such that bristles of a head portion thereof contact the dental sample received within the sample receptacle.

11 Claims, 4 Drawing Sheets

US 9,801,461 B1

ELECTRIC TOOTHBRUSH HOLDER FOR LABORATORY USE

BACKGROUND OF THE INVENTION

1. Field of the Invention

The present invention relates to a device for testing a dental appliance, and particularly to a dental testing device for laboratory use.

2. Description of the Related Art

Although holders and receptacles for toothbrushes are known, such holders and receptacles are typically designed for either personal home usage or for use during the manufacture of toothbrushes. There exists a need for a tooth brush retaining device for use in testing acrylic materials used for the construction of removable prosthetic appliances. To mimic the daily use of the prosthetic appliance, the acrylic sample needs to be brushed in the lab the same way a potential user of the appliance would. An electric toothbrush is typically used during such laboratory testing of the appliance. Generally, laboratory toothbrush holders used for such purposes are large machines that are expensive to operate. As such, there is a need for a simple device to hold a toothbrush and a sample dental appliance in place while the toothbrush is being operated to clean the dental appliance. Thus, an electric toothbrush holder for laboratory use solving the aforementioned problems is desired.

SUMMARY OF THE INVENTION

The electric toothbrush holder for laboratory use is a holder for the testing of dental appliances. The electric toothbrush holder for laboratory use includes a base having opposed upper and lower surfaces, with the lower surface being adapted for positioning on a support surface, such as a table or the like. A sample receptacle is mounted on the upper surface of the base, preferably such that the sample receptacle is vertically adjustable with respect to the base. The sample receptacle defines an open interior region for removably receiving a dental sample.

At least one support is mounted on the upper surface of the base for releasably supporting a gripping portion of an electric toothbrush. At least one bracket or the like is pivotally secured to the at least one support for releasably securing the gripping portion of the electric toothbrush to the at least one support. In use, the gripping portion of the electric toothbrush is releasably secured to the at least one support such that bristles of a head portion of the electric toothbrush contact the dental sample removably received within the open interior region of the sample receptacle.

These and other features of the present invention will become readily apparent upon further review of the following specification.

BRIEF DESCRIPTION OF THE DRAWINGS

Similar reference characters denote corresponding features consistently throughout the attached drawings.

DETAILED DESCRIPTION OF THE PREFERRED EMBODIMENTS

Figure 1:
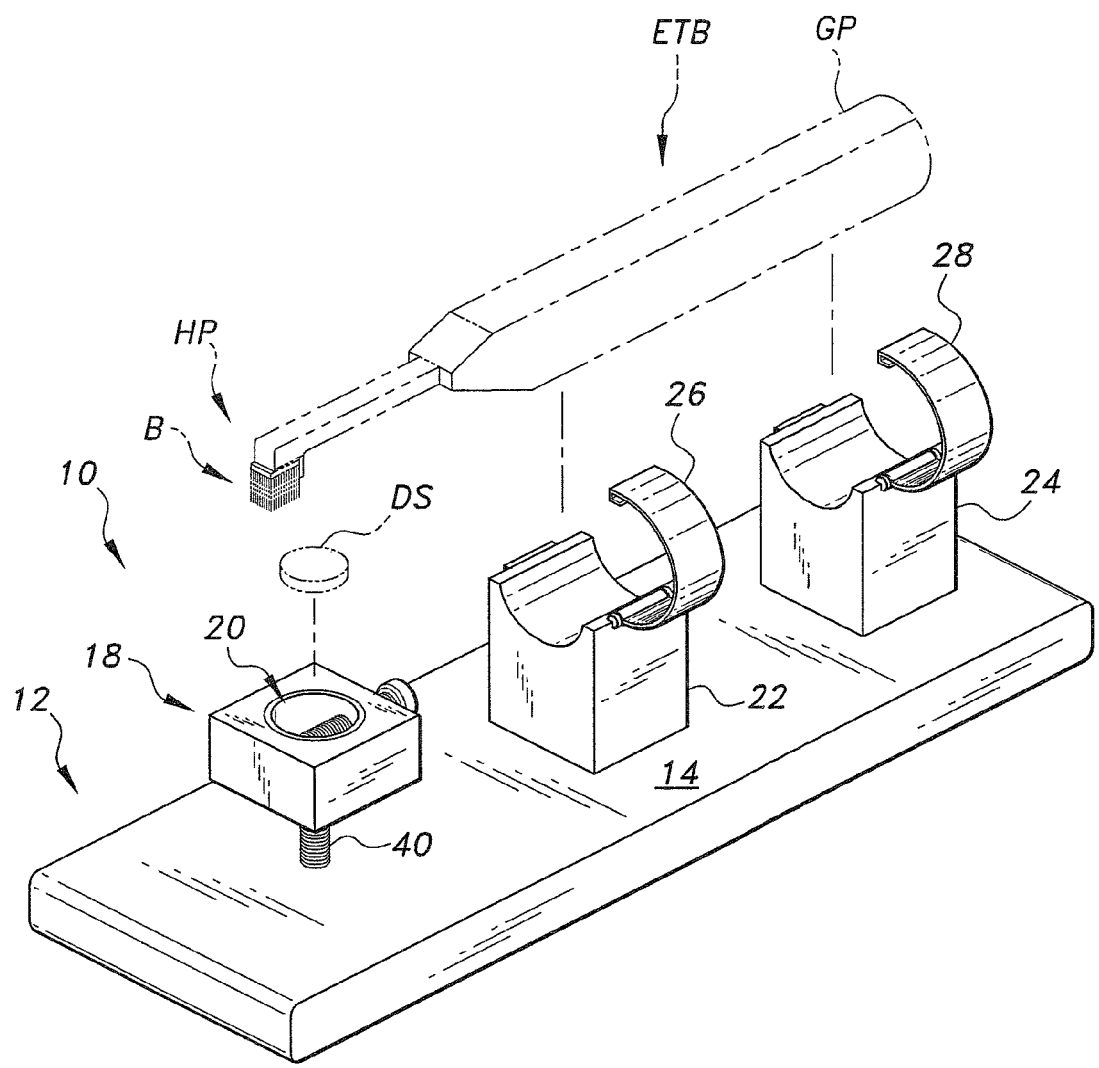
FIG. 1 is a perspective view of an electric toothbrush holder for laboratory use according to the present invention.
Figure 2:
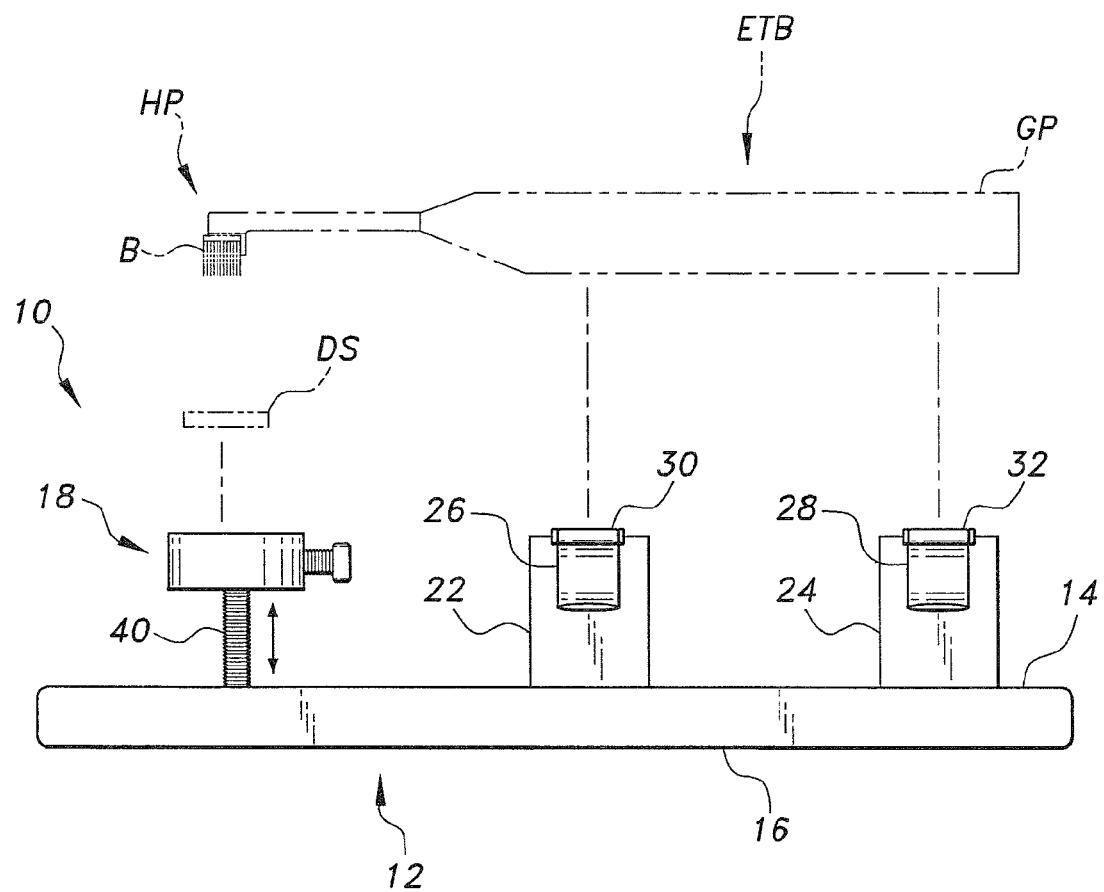
FIG. 2 is a side view of an electric toothbrush holder for laboratory use according to the present invention.

The electric toothbrush holder for laboratory use 10 is configured to hold an electric toothbrush ETB and a sample dental appliance in place during brushing of the sample dental appliance by the ETB shown in FIGS. 1 and 2. The electric toothbrush holder for laboratory use 10 includes a base 12 having opposed upper and lower surfaces 14, 16, respectively, with lower surface 16 being adapted for positioning on a support surface, such as a table or the like. A sample receptacle 18 is mounted on the upper surface 14 of the base 12, preferably such that the sample receptacle 18 is vertically adjustable with respect to the base 12. As best shown in FIGS. 1 and 2, a threaded post 40 or the like may be used to support the sample receptacle 18 on the base 12, allowing the sample receptacle 18 to be rotated and thus vertically adjusted (or vertically adjusted via any other suitable means) with respect to the base 12.

Figure 4:
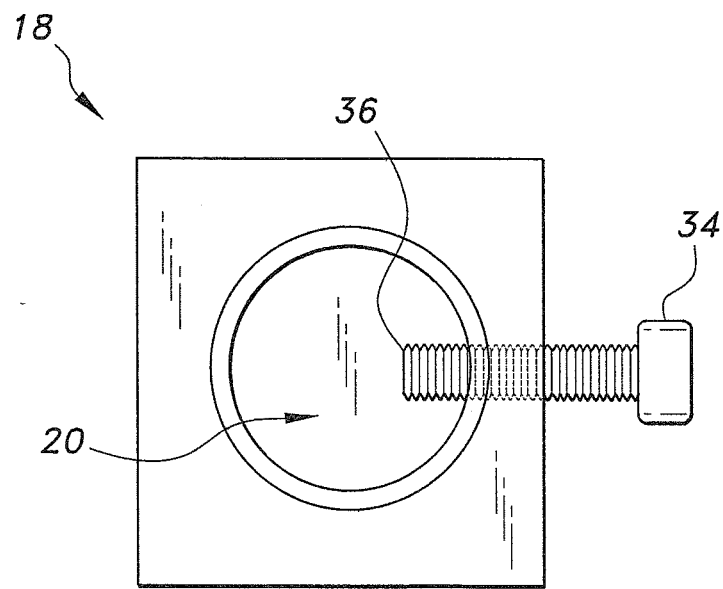
FIG. 4 is a top view of a sample receptacle of the electric toothbrush holder for laboratory use.

As best seen in FIGS. 1 and 4, the sample receptacle 18 defines an open interior region 20 for removably receiving a dental sample DS. The circular open interior region 20 is configured for reception of a dental sample, such as a removable dental prosthetic. The overall contouring and relative dimensions of the open interior region 20 may be varied dependent upon the particular dental sample tested. Additionally, it should be understood that the substantially square contouring of the sample receptacle 18 and the substantially rectangular contouring of the base 12 are shown for exemplary purposes only.

Figure 3:
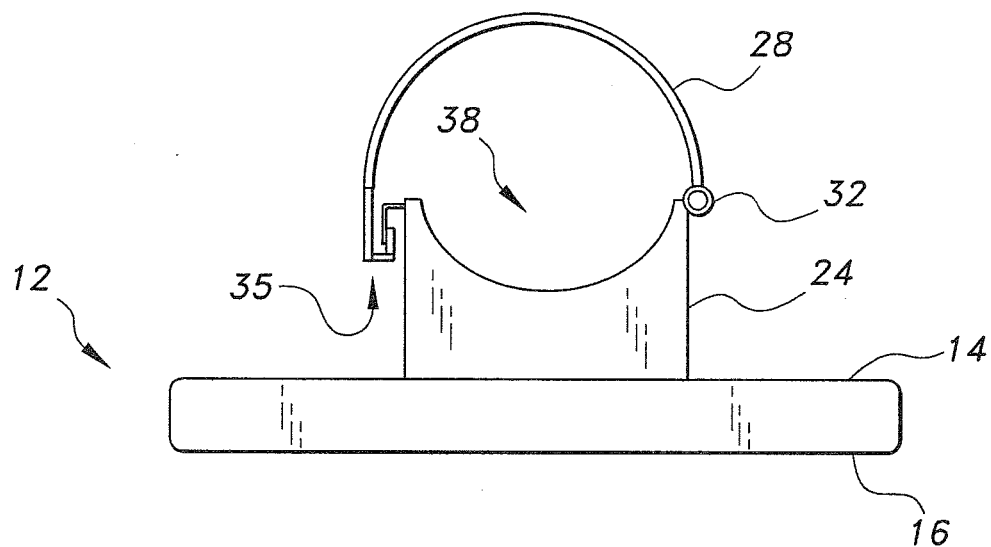
FIG. 3 is a side view of a support of the electric toothbrush holder for laboratory use.

At least one support is mounted on the upper surface 14 of the base 12 for releasably supporting a gripping portion GB of an electric toothbrush ETB. Preferably, as shown, a pair of supports 22, 24 are mounted on upper surface 14 of base 12, allowing for stable horizontal positioning of the gripping portion GP of electric toothbrush ETB. Preferably, as shown in FIG. 3, an upper surface 38 of each support has a concave contouring, matching the contouring of gripping portion GP of electric toothbrush ETB. It should be understood that the electric toothbrush holder for laboratory use 10 may be manufactured with other contouring of upper surface 38, or any other surface, dependent upon the types of electric toothbrushes used.

At least one bracket or the like is pivotally secured to the at least one support for releasably securing the gripping portion GP of the electric toothbrush ETB to the at least one support. In the Figures, a pair of brackets 26, 28 are shown to match the exemplary pair of supports 22, 24, with each being secured to its respective support by a respective hinge 30, 32 or the like. As shown, each of brackets 26, 28 has a substantially semi-circular contour to mate with the substantially circular gripping portion GP of electric toothbrush ETB, however, as noted above, the electric toothbrush holder for laboratory use 10 may be manufactured with other contouring of brackets 26, 28, or any other elements, dependent upon the types of electric toothbrushes to be used. It should be further understood that the electric toothbrush holder for laboratory use 10 may be manufactured from any suitable type of cleanable and non-corrosive material, such as stainless steel or the like.

Figure 5:
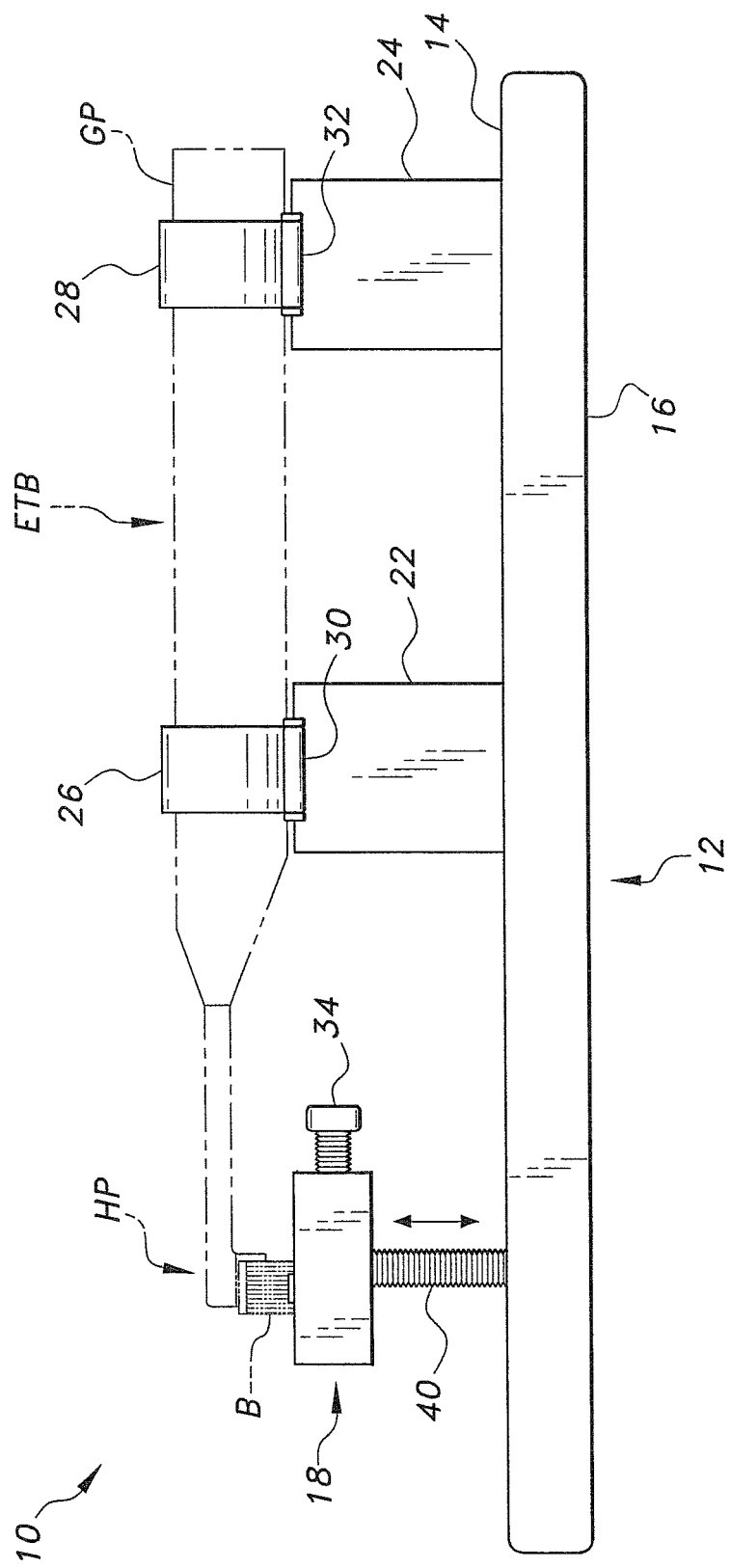
FIG. 5 is a side view of the electric toothbrush holder for laboratory use in operation.

As best shown in FIG. 3, each bracket 26, 28 is selectively and releasably lockable with respect to its corresponding support 22, 24 by a clasp 35 or the like. It should be understood that brackets 26, 28 may be releasably locked to supports 22, 24 by any suitable type of releasable lock, clasp, clamp, hook or the like. In use, as shown in FIG. 5, the gripping portion GP of the electric toothbrush ETB is releasably secured to supports 22, 24 by brackets 26, 28 such that electric toothbrush ETB is arranged with the bristles B of a head portion HP thereof contacting the dental sample DS, which is removably received within the open interior region 20 of the sample receptacle 18 for contacting the electric toothbrush ETB.

As best shown in FIG. 4, the dental sample DS may be adjustably and releasably secured within the open interior region 20 of sample receptacle 18. A threaded screw 34 or the like extends through a wall of the sample receptacle 18 such that an engaging end 36 thereof is positioned within the open interior region 20 to contact against dental sample DS. It should, however, be understood that any suitable type of adjustable retainer may be used to releasably engage and secure the dental sample DS within the receptacle 18. Thus, in order to use the electric toothbrush holder for laboratory use 10 with a variety of different electric toothbrushes and with a variety of different dental samples, threaded screw 34, or the like, may be used to adjustably secure the dental sample DS within open interior region 20 of sample receptacle 18, and the sample receptacle 18 may be vertically adjusted, by threaded post 40 or the like, in order to ensure contact between bristles B and the dental sample DS.

It is to be understood that the present invention is not limited to the embodiments described above, but encompasses any and all embodiments within the scope of the following claims.

I claim:

1. An electric toothbrush holder for laboratory use, comprising:
    a base having opposed upper and lower surfaces;
    a sample receptacle mounted on the upper surface of said base, said sample receptacle defining an open interior region for removably receiving a dental sample, wherein said sample receptacle has a vertically adjustable height with respect to said base;
    at least one support mounted on the upper surface of said base for releasably supporting a gripping portion of an electric toothbrush; and
    at least one bracket for releasably securing the gripping portion of the electric toothbrush to the at least one support,
    whereby the gripping portion of the electric toothbrush is releasably secured to the at least one support such that bristles of a head portion of the electric toothbrush contact the dental sample removably received within the open interior region of said sample receptacle.

2. The electric toothbrush holder for laboratory use as recited in claim 1, wherein the at least one bracket is pivotally secured to the at least one support.

3. The electric toothbrush holder for laboratory use as recited in claim 2, wherein the at least one bracket is selectively and releasably lockable with respect to the at least one support.

4. The electric toothbrush holder for laboratory use as recited in claim 1, wherein the sample receptacle includes an adjustable retainer to releasably retain and secure the dental sample within the open interior region of said sample receptacle.

5. The electric toothbrush holder for laboratory use as recited in claim 4, wherein the adjustable retainer of said sample receptacle comprise a threaded screw extending through a wall of said sample receptacle, such that an engaging end thereof is positioned within the open interior region.

6. The electric toothbrush holder for laboratory use as recited in claim 1, wherein an upper surface of the at least one support has a concave contour.

7. An electric toothbrush holder for laboratory use, comprising:
    a base having opposed upper and lower surfaces;
    a sample receptacle mounted on the upper surface of said base, said sample receptacle defining an open interior region for removably receiving a dental sample, wherein said sample receptacle has a vertically adjustable height with respect to said base;
    at least one support mounted on the upper surface of said base for releasably supporting a gripping portion of an electric toothbrush; and
    at least one bracket pivotally secured to the at least one support for releasably securing the gripping portion of the electric toothbrush to the at least one support,
    whereby the gripping portion of the electric toothbrush is releasably secured to the at least one support such that bristles of a head portion of the electric toothbrush contact the dental sample removably received within the open interior region of said sample receptacle.

8. The electric toothbrush holder for laboratory use as recited in claim 7, wherein the at least one bracket is selectively and releasably lockable with respect to the at least one support.

9. The electric toothbrush holder for laboratory use as recited in claim 7, further comprising an adjustable retainer for releasably securing the dental sample within the open interior region of said sample receptacle.

10. The electric toothbrush holder for laboratory use as recited in claim 9, wherein the adjustable retainer comprises a threaded screw extending through a wall of said sample receptacle, such that an engaging end thereof is positioned within the open interior region.

11. The electric toothbrush holder for laboratory use as recited in claim 10, wherein an upper surface of the at least one support has a concave contour.

* * * * *